(12) United States Patent
Ollivier

(10) Patent No.: US 6,575,759 B1
(45) Date of Patent: Jun. 10, 2003

(54) RAPID LOCKING CONNECTOR HEAD FOR ACTIVE IMPLANTABLE MEDICAL DEVICES

(75) Inventor: Jean-François Ollivier, Villiers-le-Bade (FR)

(73) Assignee: ELA Medical S.A., Montrouge (FR)

( * ) Notice: Subject to any disclaimer, the term of this patent is extended or adjusted under 35 U.S.C. 154(b) by 0 days.

(21) Appl. No.: 09/551,891

(22) Filed: Apr. 19, 2000

(30) Foreign Application Priority Data

Apr. 19, 1999 (FR) .......................................... 99 04863

(51) Int. Cl.[7] .............................................. H01R 13/62
(52) U.S. Cl. .......................................... 439/2; 439/346
(58) Field of Search .................................. 439/346, 372

(56) References Cited

U.S. PATENT DOCUMENTS

| | | | |
|---|---|---|---|
| 3,891,289 A | * 6/1975 | Hanke | 439/346 |
| 4,061,409 A | * 12/1977 | Bealmear | 439/346 |
| 4,167,658 A | * 9/1979 | Sherman | 439/346 |
| 5,082,453 A | 1/1992 | Stutz, Jr. | 439/265 |
| 5,545,188 A | 8/1996 | Bradshaw et al. | 607/37 |

FOREIGN PATENT DOCUMENTS

| | | | |
|---|---|---|---|
| EP | 0 402 681 | 12/1990 | |
| JP | 405021109 | * 1/1993 | 439/346 |
| SU | 1557608 | * 4/1990 | 439/346 |

* cited by examiner

*Primary Examiner*—P. Austin Bradley
(74) *Attorney, Agent, or Firm*—Orrick, Herrington & Sutcliffe LLP

(57) ABSTRACT

A connector system for an active implantable medical device including a generator and a connector head (10) equipped with a plurality of parallel axial cavities (12) receiving respective probe connectors (14), and a reversible means for mechanical tightening of each probe connector in its cavity. The tightening can be obtained by retractable elements (32) actuated simultaneously by a common element (36, 38, 40) movable between two positions, one locked and the other unlocked. The retractable elements project radially inside each respective cavity when the common element is in a locked position to exert a radial contact pressure on each probe connector insert therein, preferably on electrically insulating areas (20, 22) of the probe connectors. The retractable elements (32) are preferably carried by a common barrel (28) movable in rotation around a central axis of the connector head.

7 Claims, 2 Drawing Sheets

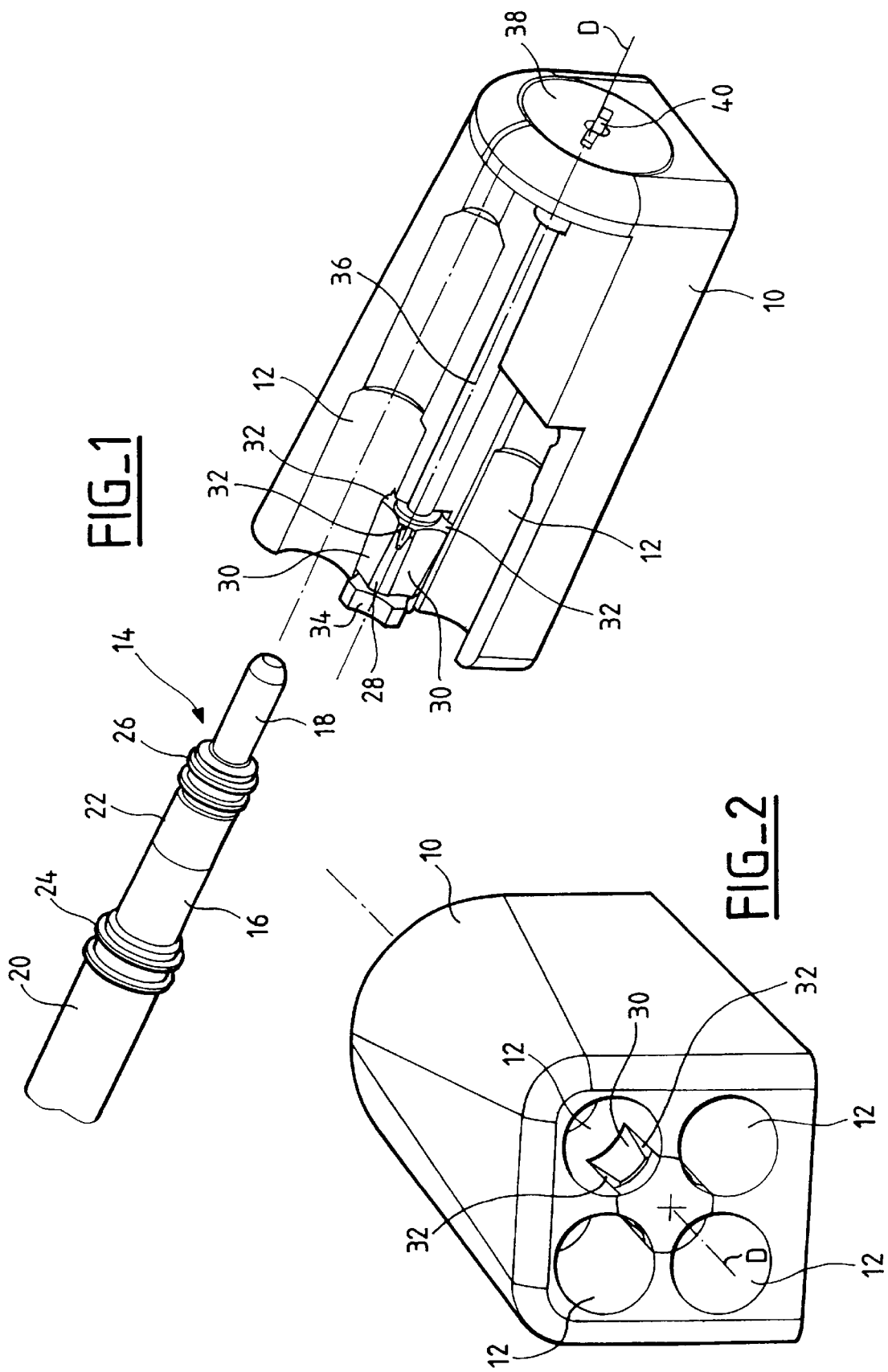

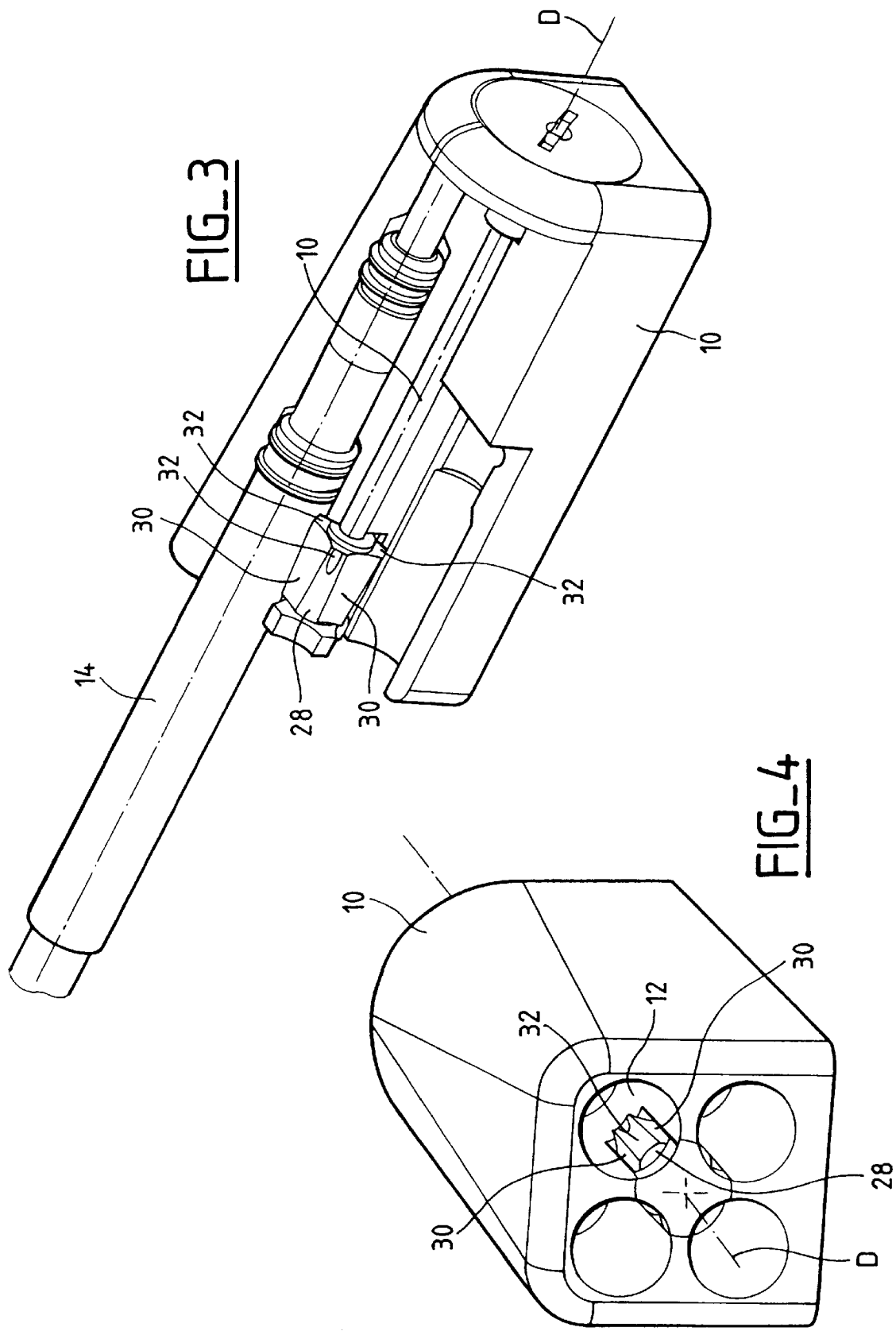

RAPID LOCKING CONNECTOR HEAD FOR ACTIVE IMPLANTABLE MEDICAL DEVICES

FIELD OF THE INVENTION

The present invention relates to connectors for active implantable medical devices. Although the invention is mainly described in the context of connectors for pacemakers, it should be understood that this is only one embodiment of the invention. The invention is applicable more generally to a wide variety of "active implantable medical devices" as such devices are defined by the Jun. 20, 1990 Director No. 90/385/CE of the Council of the European Communities. This definition of active implantable medical devices includes, in addition to pacemakers, defibrillators and/or cardiovertors, neurological devices, diffusion pumps delivering medical substances, cochlear implants, implanted biological sensors, etc.

BACKGROUND OF THE INVENTION

Active implantable medical devices typically comprise a case, also called a housing, containing the electronics of the devices. In the case of cardiac devices, the case is generally referred to as a "generator" or "pulse generator". The electronics inside the case are electrically and mechanically connected to one or more probes exterior to the case.

More specifically, the device case has a body containing the various electronic circuits and a power supply for the device, and a connector head that is fixed to the case and equipped with one or more cavities able to receive one or more probes.

In this regard, reference can be made to the French and European standard NF EN 50007 entitled "Connector with Low Profile for Implantable Pacemaker", which defines a standardized connection known as "IS-1". This standard makes it possible to guarantee the interchangeability of the probes and the pulse generators respectively produced by numerous different manufacturers. As noted, the invention is not intended to be limited to the particular case of the connection systems according to this standard, nor even to the case of connection systems for pacemakers.

Usually, the connection between a probe and the connector head of the generator is carried out by one or more screws, tightened by the surgeon using an ad hoc tool, such as a screwdriver provided with a torque limiter. The connection is made at the time of implantation.

However, forming the connection by tightening a screw presents several disadvantages. First, in addition to requiring provision of a specific tool for this purpose, this known technique also requires the presence of a plug that permits the passage of the tool through the plug in a close frictional fit. This is so that after the end of the probe is inserted in the connector cavity, the screw is tightened and the tool is withdrawn, the plug reseals to prevent the head from coming into contact with organic fluids. This requirement that the plug be penetrable to permit the tool to enter for tightening the screw and then reseal after removal of the tool presents an additional cost of manufacture and an increase in the volume of the generator with respect to the size of the connector head.

Second, this known connection system suffers from a risk that the surgeon will not tighten the screw properly, and either tighten the screw too much and damage the device or insufficiently tighten the screw, thus leaving the probe at risk of disconnecting. The point of proper tightening is all the more critical since there is no visual means to verify that the tightening has been correctly performed.

The disadvantages of this known connection system are particularly amplified in the case of implantable devices using a large number of probes, for example, three, four, and even more probes, as in the case of the so-called enslaved (rate responsive) devices requiring an external physiological sensor(s), and "triple chamber", "quadruple chamber" and "multisite" cardiac devices requiring the implantation, and thus connection, of detection and/or stimulation electrodes in several locations of the myocardium. These known sensors, detection electrodes and stimulation electrodes are types of probes as the term "probe" is used herein.

Thus, an implant designed to receive four probes would include eight screws, which implies, on a mechanical level, a bulky and complex structure for the connector head. Moreover, the structure is rather delicate to use. For example, at the time of the implantation, the surgeon must tighten all eight screws properly, without undertightening or overtightening of same.

OBJECTS AND SUMMARY OF THE INVENTION

It is, therefore, an object of the invention to overcome the various disadvantages of the known connection systems by providing an improved connection system having a connector head structure that is simple to manufacture and easy to use by the practitioner.

More particularly, the invention is useable as part of an implantable active medical device of the generic type, including a generator and a connector head equipped with a plurality of parallel axial cavities receiving respective probes, more specifically a connector component of the probe which may be in the form of an electrically conductive cylindrical pin, and reversible means for tightening mechanically each probe connector head within its cavity in the connector head.

Broadly speaking, according to the invention, the means for tightening mechanically includes retractable elements actuated simultaneously by a common action element movable between two positions, one locked and the other unlocked. In the locked position, the retractable elements project inside each respective cavity to exert a contact pressure, preferably radially project to exert a radial contact pressure, on each probe connector component inserted into its respective cavity. In the unlocked position, the probe connector may pass unobstructedly into and out of its corresponding cavity.

In the case that the probe connector components are of the type which comprise an electrically insulated area adjacent an annular cylindrical conducting element, or interposed between two cylindrical conducting elements, in which examples the insulating sheath and the conducting elements are preferably annular cylindrical lengths, the retractable elements preferentially exert a radial pressure on the electrically insulated area. Similarly, if more than one electrically insulated area exists, multiple retractable elements exerting pressure on one or more of the insulating areas can be used.

In a preferred embodiment, the probe connector component includes a sealing element (also called a sealing relief) protruding from the annular surface which engages the connector head cavity to form a seal, and the retractable elements project into an area of the probe which is distal to the sealing relief. More than one sealing relief can be used.

In one advantageous embodiment of the connector system, the axial female cavities are distributed regularly about and at the same distance from a central axis of the connector head, the central axis being parallel to the axes of the cavities. In this embodiment, the retractable elements are carried by a common barrel that is movable around the central axis. The retractable elements are advantageously made out of an elastically deformable material, for example, a silicone.

BRIEF DESCRIPTION OF THE DRAWINGS

Further features, characteristics, and advantages of the present invention will become apparent to a person of ordinary skill in the art from the following detailed description of a preferred embodiment of the present invention, made with reference to the annexed drawings, in which the same numeral references refer to like elements, and in which:

FIG. 1 is an elevated perspective view of a connector head according to a preferred embodiment of the invention, showing a probe extremity before insertion;

FIG. 2 is an elevated perspective view of the connector head of FIG. 1, taken from the cavity side in an unlocked position allowing for the insertion of the probe into the connector head;

FIG. 3 is a partial sectional view of FIG. 1, after insertion of a probe into the connector head; and FIG. 4 is a view of FIG. 2 in the locked position.

DETAILED DESCRIPTION OF THE DRAWINGS

With reference to FIGS. 1–4, reference 10 indicates in a general way a connector head according to the present invention, which is made out of rigid insulating material such as an epoxy resin. This contrasts with prior known connector heads that are usually made out of a flexible material, such as a silicone resin. Head 10 is equipped with one or more, preferably a plurality of, cavities 12. In the illustrated example, four cavities are shown.

These four cavities extend along parallel axes and are regularly distributed around a central axis D of head 10. Stated otherwise, axis D is parallel with the axes of cavities 12 and is located at the same distance therefrom.

Each cavity 12 receives the proximal end of a probe (i.e., the end provided with the connection component that couples the probe to the generator of the implant), for example, a probe in conformity with mechanical dimensions of standard IS-1, mentioned above. As noted, the invention has the advantage of being entirely compatible with this standard IS-1, which enables the implantable devices to accept without modification all the current or future probes satisfying this standard.

The end of probe 14 comprises, for example, two annular cylindrical conducting components 16 and 18, surrounded by insulating areas 20, 22. Insulating areas 20, 22 are typically made of a flexible material such as a silicone resin.

The insulating areas are generally equipped with an annular sealing relief 24, 26 intended to cooperate in close frictional and sealing contact with the interior wall of the corresponding cavity 12.

Each cavity 12 contains one or two terminals (according to whether the corresponding probe is unipolar or, as illustrated, bipolar) ensuring the electric connection between the conducting element 16 or 18 and an input/output circuit of the generator of the implantable device. Inasmuch as the invention is not directed to the electric connection of the probe to the connector head and is independent of the technique chosen to ensure the electric connection, of which suitable techniques are known in the art, these issues are not discussed in more detail herein. The invention is instead directed to the mechanical stability and integrity of the connector head to the ends of the various probes once all of the probes have been inserted in their respective cavities 12.

In the preferred embodiment illustrated, the mechanical locking connection is ensured by a central barrel 28, movable in rotation around the axis D and comprising a plurality of hollow areas 30. The plurality of hollow areas 30 are a number equal to the number of cavities 12, and are separated by an equal number of projecting elements 32 evenly distributed at the periphery around the axis D. Barrel 28 rotates around a fixed part 34, which is equipped with a bearing (not shown) receiving barrel 28 which is independent of a stem 36 that is able to be rotated by a body 38. Body 38 is equipped, for example, with a slit 40 intended to receive a drive element, such as a screwdriver. Body 38 is located along axis D at the end of the connector head 10 which is opposite to the connector head end having the openings of the cavities 12 for receiving the probe connectors 14.

Barrel 28 is susceptible to take one of two positions, respectively illustrated on FIGS. 2 and 4, with the passage from one position to the other position being carried out by a rotation, ⅛ of a turn in the illustrated example, i.e., with four cavities 12 and four corresponding projecting elements 32. In the first position—the unlocked position—illustrated in FIG. 2, the hollow areas 30, which are preferably areas having a concave cylindrical surface of the same curve as the corresponding areas of cavity 12, come to the level of the wall of cavity 12. Viewed from the exterior, each of cavities 12 is thus presented with a smooth cylindrical form, without any obstacle, thus allowing the easy insertion of the full depth of probe connector 14 into the cavity.

Once the four probe connectors have been inserted in their respective cavities 12, turning body 38 by ⅛ of a turn causes barrel 28 to assume the second and locked position, illustrated in FIG. 4. In this second position, retractable elements 32 project inside cavities 12. Because of the elongated form, projecting elements 32 come to contact along a line of the connector head in the area of the silicone insulating sleeve 20 of probe 14. Preferably, the retractable elements project radially into the cavity interior.

The silicone of the connector and/or barrel is an incompressible material (deformation with constant volume). Therefore, it is enough to construct the projecting elements 32, i.e., to choose the surface of the area in contact with the silicone sheath and the dimension of the projection, so as to obtain the desired retention force. Typically the force value is that prescribed by the standard IS-1, which defines precisely at the same time the retention force to be exerted on a connector head and the zone or area on which this force can be exerted.

In an alternative embodiment, the rotary barrel system can be replaced, among other things, by a device in which the projecting elements can be retracted or deployed inside cavity 12 by a system combining a screw (pulled by the body 38) with a spreading mechanism. In this case, the movement of the projecting elements is only by action of a radial displacement in cavity 12, without any rotation around a central axis. Other mechanical systems to deploy the retractable elements may be similarly employed.

One skilled in the art will appreciate that the present invention can be practiced by other than the described embodiment, which is presented for the purposes of illustration and not of limitation.

I claim:

1. A connection system for an active implantable medical device including a generator and a connector head, comprising a plurality of axial cavities in said connector head, each said cavity having a size for receiving a probe connector, reversible means for mechanical tightening of each probe connector in its cavity, wherein said reversible tightening means comprises a common body, movable between a locked position and an unlocked position, and a plurality of retractable elements actuated simultaneously by said common body, said retractable elements projecting inside each respective cavity in response to said common body being in said locked position, wherein said probe connector positioned in said cavity comprises at least one annular cylindrical conducting element and at least one electrically insulated area adjacent said at least one annular cylindrical conducting element, and wherein the retractable elements are positioned relative to said probe connector to project on said at least one electrically insulated area in response to said common body being in said locked position.

2. A connection system for an active implantable medical device including a generator and a connector head, the connector head comprising a plurality of axial cavities and a central axis and the plurality of axial cavities further comprising a corresponding plurality of axes disposed in parallel with and evenly distributed about and at the same distance from said central axis, each said cavity having a size for receiving a probe connector, and reversible means for mechanical tightening of each probe connector in its cavity, wherein the reversibly tightening means comprises a common body movable between a locked position and an unlocked position including a barrel on which a plurality of retractable elements are mounted and on which the retractable elements are movable in rotation around said central axis, said retractable elements projecting inside each respective cavity in response to said common body being in said locked position.

3. The connection system of claim 2 wherein said retractable elements project radially inside each respective cavity in response to said common body being in said locked position.

4. The system of claim 2, wherein the barrel is of an elastically deformable material.

5. The system of claim 4 in which the barrel is a silicone material.

6. A connection system for an active implantable medical device including a generator and a connector head, comprising a plurality of axial cavities in said connector head, each said cavity having a size for receiving a probe connector, and reversible means for mechanical tightening of each probe connector in its cavity, wherein said reversible tightening means comprises a common body, movable between a locked position and an unlocked position without axial movement of said common body, and a plurality of retractable elements actuated simultaneously by said common body, said retractable elements projecting inside each respective cavity in response to said common body being in said locked position, and further comprising a probe connector positioned in said cavity comprising an annular sealing relief in contact with an interior wall of said cavity, wherein the retractable elements are positioned relative to said probe connector to project in an area of the probe located distally of said sealing relief.

7. The connection system of claim 6 wherein said retractable elements project radially inside each respective cavity in response to said common body being in said locked position.

* * * * *